(12) United States Patent
Lin

(10) Patent No.: US 11,737,664 B2
(45) Date of Patent: Aug. 29, 2023

(54) PERIMETER

(71) Applicant: Chen Lin, Hunan (CN)

(72) Inventor: Chen Lin, Hunan (CN)

( * ) Notice: Subject to any disclaimer, the term of this patent is extended or adjusted under 35 U.S.C. 154(b) by 638 days.

(21) Appl. No.: 16/961,547

(22) PCT Filed: Aug. 1, 2018

(86) PCT No.: PCT/CN2018/097852
§ 371 (c)(1),
(2) Date: Jul. 10, 2020

(87) PCT Pub. No.: WO2019/192108
PCT Pub. Date: Oct. 10, 2019

(65) Prior Publication Data
US 2021/0059516 A1 Mar. 4, 2021

(30) Foreign Application Priority Data
Apr. 3, 2018 (CN) .................. 201820462284.X

(51) Int. Cl.
*A61B 3/00* (2006.01)
*A61B 3/024* (2006.01)
*A61B 3/113* (2006.01)

(52) U.S. Cl.
CPC .......... *A61B 3/0091* (2013.01); *A61B 3/0083* (2013.01); *A61B 3/024* (2013.01); *A61B 3/113* (2013.01)

(58) Field of Classification Search
CPC ..... A61B 3/0091; A61B 3/0083; A61B 3/024; A61B 3/113; A61B 3/10
(Continued)

(56) References Cited

U.S. PATENT DOCUMENTS 6,161,931 A 12/2000 Slishman
6,607,527 B1 * 8/2003 Ruiz .................. A61B 3/113
351/212
2011/0319873 A1 12/2011 Raski et al.

FOREIGN PATENT DOCUMENTS

CN 101342072 A 1/2009
CN 103037754 A 4/2013
(Continued)

OTHER PUBLICATIONS

International Search Report and Written Opinion issued in corresponding Application No. PCT/CN2018/097852 dated Dec. 28, 2018.

*Primary Examiner* — Mohammed A Hasan
(74) *Attorney, Agent, or Firm* — Ditthavong, Steiner & Mlotkowski

(57) ABSTRACT

A perimeter, including two types: one is a fixation forcing perimeter, and the other is an objective perimeter combined with electro-physiology under forced fixation; the perimeter comprises a fixation forcing device, a display conduction device, a perimetry display device, a feedback device for recording feedback information, and a control center for controlling the perimetry display device and collecting feedback information; the fixation forcing device comprises a negative pressure ring (2) and a negative pressure tube (3), and is adsorbed to the eyeball by negative pressure; when the eyeball moves, the fixation forcing device moves synchronously, and the fixation is forced at the same position, thereby eliminating the influence of a fixation point on the examination results of the perimeter; in the objective perimeter, an electro-physiological signal after forced fixation is automatically recorded by an electro-physiological instrument, so that the subjective response of a patient is eliminated, and the examination results are objective; and the (Continued)

change in the field of view can be early discovered using the electro-physiological signal as an analysis indicator.

7 Claims, 2 Drawing Sheets

(58) Field of Classification Search
USPC .......................................................... 351/224
See application file for complete search history.

(56) References Cited

FOREIGN PATENT DOCUMENTS

| | | | |
|---|---|---|---|
| CN | 206026294 U | * | 3/2017 |
| CN | 206026294 U | | 3/2017 |
| JP | 2005143684 A | | 6/2005 |
| JP | 2016198387 A | | 12/2016 |

* cited by examiner

PERIMETER

CROSS-REFERENCE TO RELATED APPLICATIONS

The present application is a U.S. National Phase of PCT/CN2018/097852 filed on Aug. 1, 2018 claiming priority to Chinese Patent application No. 201820462284.X filed Apr. 3, 2018. The entire disclosure of the PCT Application is hereby incorporated by reference into the present Application.

FIELD OF THE INVENTION

The present invention relates to a perimeter for measuring the field of view of a testee.

BACKGROUND OF THE INVENTION

The field of view refers to a range of space that can be seen when the head and the eyeballs are immobile and the eyes view an object in front, the size and shape of the field of view are related to the distribution of sensory cells on the retina, and the field of view can be measured by a perimeter. As one of the main clinical methods for visual function detection in ophthalmology, perimetry plays an important role in the diagnosis and follow-up of eye diseases such as glaucoma and optic nerve diseases. The perimetry includes kinetic perimetry and static perimetry. Kinetic perimetry: i.e., a conventional perimetry, in which test marks of different sizes are moved from different peripheral directions to the center, points where a patient can just feel the appearance or disappearance of the test marks are recorded, these points with the same light sensitivity constitute an isopter of test mark detection, and a similar "visual island" is drawn with several kinds of isopters measured by different test marks. The kinetic perimetry has the advantages of high speed and application to peripheral field of view, but has the disadvantage of low discovery rate of small and paracentral relative scotoma. Static perimetry: at each set point of a screen, the brightness of test marks is increased from weak to strong, and the brightness that a patient can just feel is a retinal sensitivity or threshold at that point. At present, the perimetry used in clinical practice is psychophysical examination, which reflects the subjective feeling of a patient.

Current computer automated perimeters used in clinical practice are mainly for the diagnosis and follow-up of glaucoma and partial retinal optic nerve diseases. However, for some early or clinically asymptomatic ocular diseases, the earliest defect changes of the field of view still cannot be found by the conventional computer perimetry. Therefore, ophthalmic researchers have been trying to develop a novel perimeter to achieve earlier, more stable, more sensitive and more specific detection of pathological changes. A variety of new perimetry methods currently developed, including short wavelength perimetry, kinesthetic perimetry, frequency-doubled perimetry, high-pass resolution and model discrimination perimetry, automatic pupil perimetry, flicker perimetry, micro-perimetry, etc., are specially designed to reflect visual impairment characteristics of different eye diseases. These novel perimeters have improved the performance of the conventional perimeters to a certain extent through different principles, but still have the following problems:

First, influence of a fixation point: in the process of measurement, due to the long examination time and the influence of surrounding signals, it is difficult for a patient to concentrate on the fixation point, observe surrounding signal lights, and make a response in time and press a signal collector. The patient always suffers from the deviation from the fixation point, which affects the accuracy and repeatability of examination results. Although the tracking technology is used in some examination devices, the projection position of view signals can be automatically adjusted with the movement of the fixation point, but the signal adjustment of a computer still lags behind the movement of the fixation point of human eyes, and it is still difficult to fundamentally eliminate the influence due to changes of the fixation point. In addition, since the micro-perimeter cannot achieve long-term fixation, it is difficult to acquire a super-large amount of data during rapid repeated stimulation, and it is impossible to acquire more accurate electro-physiological data.

Second, influence of patients' subjectivity: different patients' responses to the stimulation are different, some patients can make a response in time and press the signal collector after viewing the signal lights, but some patients have a slow response, do not make a response in time after viewing the signal lights, and press the signal collector when the signal lights are on next time, resulting in wrong examination results.

In order to reduce the adverse influences, the current computer automated perimeter is designed with a "capture experiment" program to detect the false positive rate, false negative rate and fixation loss rate in each test. In order to avoid the influence of mechanical sound and patient habits, the computer automated perimeter produces a mechanical sound proportionally without light stimulation, and if the patient responds, the test result is false positive. An extremely bright light stimulus is present in the area where the threshold has been established. If the patient is unable to respond, it indicates that the patient is distracted and the test result is false negative. When photo-electricity is randomly projected into a physiological blind area, if the number of times the patient responds exceeds a certain limit, there is no central fixation. This method can reduce the influences of the fixation point and the patient's subjective operation, but still cannot solve the problem fundamentally, resulting in the deficiencies of repeatability, specificity, sensitivity and accuracy.

The eyeball is a bipolar ball. The cornea presents a positive potential relative to the retina, and there is a potential difference between the cornea and retina, thus forming an electric field around the eye. When the eyeball rotates, the spatial phase of the electric field is changed. Eye movement can produce bio-electricity, so a potential difference exists between the cornea and the retina, and the cornea is positively charged with respect to the retina. When the eye is gazing at the front without moving, a stable reference potential can be recorded. When the eye moves in the horizontal direction, the potential difference between the left and right skin of the eye is changed. When the eye moves in the vertical direction, the upper and lower potentials of the eye are changed. The change in potentials is guided into an amplifier by an electrode placed at a corresponding position of the skin, and an electro-oculogram signal is displayed by a galvanometer with the amplifier or displayed on an oscilloscope. A visual electro-physiological instrument can objectively provide a diagnosis basis for diseases at each layer of the retina and each segment of the visual pathway by analyzing the bio-electrical changes of the visual system for light stimulation, reflecting the functional statuses of the retina and the visual pathway, and adjusting the stimulation condition and acceptance way. At present, the electro-physiological examination technology is applied to the early detection of glaucoma in clinical practice. Judging the impairment or progression of the glaucoma is mainly through the waveform of an electro-physiological signal. Although the objective examination device can objectively reflect the patient's retinal impairment, the patient is required to always gaze at the screen during the whole examination, and the change in patient's eye position may cause the waveform to change, so that multiple examination results of the same patient may be greatly different. In addition, the waveform varies among different individuals of crowds, and it is difficult to determine the normal value, abnormal range and other issues, so the electro-physiological examination technology is hardly really applied to the detection of glaucoma.

SUMMARY OF THE INVENTION

In order to solve the above technical problems, the present invention is directed to provide a perimeter capable of eliminating the influence of a fixation point on perimetry. The specific technical solution is as follows.

A perimeter is divided into two types according to different feedback devices: one is a fixation forcing perimeter, and the other is an objective perimeter combined with electro-physiology under forced fixation. The perimeter includes a fixation forcing device, a display conduction device, a perimetry display device, a feedback device for recording feedback information, and a control center for controlling the perimetry display device and collecting feedback information, wherein the fixation forcing device is used for forcing the eyeball in a fixation state during perimetry, and the display conduction device is connected to the fixation forcing device and the perimetry display device respectively. The fixation forcing device is adsorbed to the eyeball of a testee by negative pressure, the eye can observe the perimetry display device through the display conduction device, the control center controls images displayed on the perimetry display device through a predetermined control program, the testee makes corresponding feedbacks according to the changing images on the perimetry display device, the feedback information is recorded in the feedback device, and the testee's field of view is measured accordingly. The relative positions of the fixation forcing device and the eyeball are fixed, the relative positions of the perimetry display device and the fixation forcing device are fixed, and when the eyeball moves, the relative positions of the gazed perimetry display device and the eyeball do not change, thereby eliminating the influence of the fixation point of the conventional perimeter on the results, and improving the accuracy and repeatability of the perimetry.

In the above technical solution, the fixation forcing device includes a negative pressure ring, a hole is formed in the middle of the negative pressure ring, and the display conduction device is fixedly arranged at the hole. The negative pressure ring is connected to a negative pressure device through a negative pressure tube to form certain negative pressure between the eyeball and the negative pressure ring, thereby fixing the negative pressure ring to the eyeball. When the test is over, the negative pressure device is closed to remove the negative pressure ring from the eyeball. In the above technical solution, the fixation forcing device includes a negative pressure ring and a negative pressure tube connected to the negative pressure ring, an observation cylinder is connected to the middle of the negative pressure ring, one end of the observation cylinder is connected to the middle of the negative pressure ring, the display conduction device is fixedly arranged at the other end of the observation cylinder, and the display conduction device can conduct images on the perimetry display device. The observation cylinder is provided with an observation hole in the center, and a lens set is arranged in the observation hole. The negative pressure ring is forcibly fixed on the eyeball, the testee gazes at the perimetry display device through the observation cylinder and the display conduction device, the negative pressure ring adsorbed to the eyeball can move synchronously with the rotation of the eyeball without adjusting the illumination angle, the images are always in front of the eye, and the patient only needs to respond to the light stimulus without distracting to perform fixation on a certain point. Since the relative positions of the eyeball and the perimetry display device are fixed, after the influence of the fixation point on the patient's examination result is eliminated, the perimetry is greatly improved in terms of repeatability, specificity, sensitivity and accuracy.

In the above technical solution, the display conduction device includes two types, one type includes a projection screen and light guide fibers connected to the projection screen, the projection screen is connected to the fixation forcing device, one ends of the light guide fibers are connected to the projection screen, and the other ends are connected to the perimetry display device to project an image on the perimetry display device into the eye; the other type includes only light guide fibers, the light guide fibers are arranged in a certain way and connected to the fixation forcing device, and the other ends are connected to point light sources to directly project light points of the point light sources into the eye.

In the above technical solution, for the fixation forcing perimeter, the feedback device is a signal collector, and when the testee observes the image on the perimetry display device, the testee triggers the signal collector to record the feedback information of the testee.

In the above technical solution, for the objective perimeter, the feedback device is an electro-physiological examination instrument for recording an electro-physiological signal generated when the testee observes an image on the perimetry display device, thereby examining the testee's field of view. After the negative pressure ring is fixed to the eyeball, the testee is forced to perform fixation on the perimetry display device, which can enhance the time, frequency and range of light stimulation and realize repeated stimulation of single-point light similar to the perimetry. The patient's field of view is judged by analyzing the frequency and time of stimulation of the single-point light and whether the patient produces electro-physiological signals, and any operation of the patient is not required in such a mode, thereby eliminating the influence of the fixation point and the testee's subjective operation, obtaining a real objective perimeter, and greatly improving the accuracy and repeatability of physical examination.

In the above technical solution, the control center is a computer loaded with an artificial intelligence algorithm, and can automatically perform personalized display adjustment according to the age of the patient and the previous examination status and perform personalized processing on the collected feedback data. The personalized display adjustment includes highlighting a previous blind area of the field of view and/or a possible blind area.

Technical Effects

1. The display conduction device is adsorbed to the eyeball by using the negative pressure device, images are transmitted through the light guide fibers, and the position of the perimetry display device relative to the eyeball is fixed and is constantly in front of the eyeball, thereby eliminating the influence of the fixation point on the examination results of the perimeter.

2. An observation hole with a constant inner diameter is formed in the center of the negative pressure ring, which can ensure that all patients are examined under the same diameter of the observation hole, is beneficial to comparative observation between different patients and comparative observation of the same patient in different periods to judge the outcome of the disease.

3. The perimeter can be combined with an electro-physiological examination instrument. The conventional electro-physiological examination instrument cannot acquire corresponding electro-physiological signals because the single-point stimulation is too weak, and infinite times of signal superposition at the same position are difficult to achieve due to the influence of the fixation point. In the present invention, the fixation point is fixed, and single-point stimulation signals that are acquired by infinite times of single-point repetition can be infinitely amplified to obtain clear electro-physiological signals. After combined with the electro-physiological instrument, the perimeter can achieve a major breakthrough in perimetry, that is, achieve objective perimetry.

Figure 1:
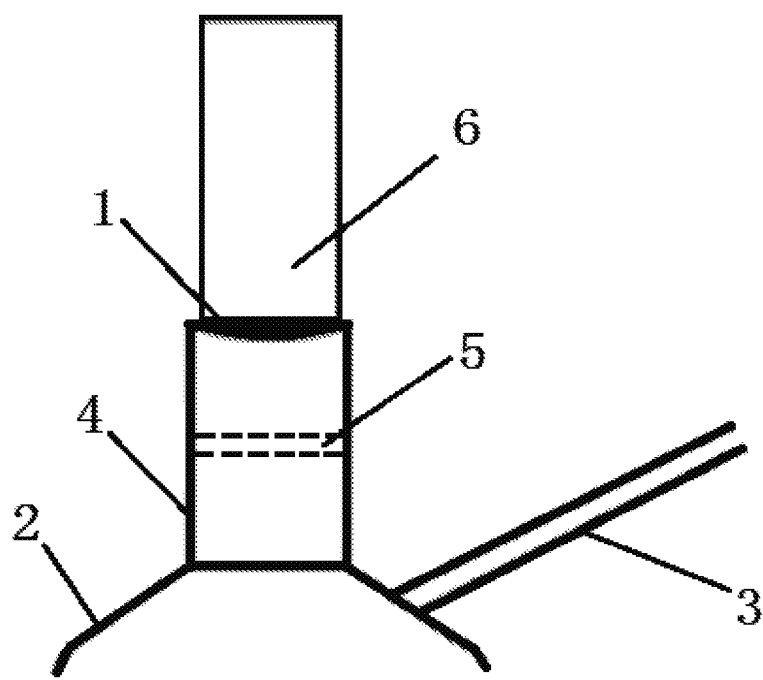
FIG. 1 is a schematic diagram of an adsorption device of the present invention.

In which: projection screen 1, negative pressure ring 2, negative pressure tube 3, observation cylinder 4, lens set 5, light guide fiber 6, button 7, multifunctional chair 8, support rod 9.

DETAILED DESCRIPTION OF EMBODIMENTS

The present invention will be further described in detail below in combination with the accompanying drawings.

Figure 2:
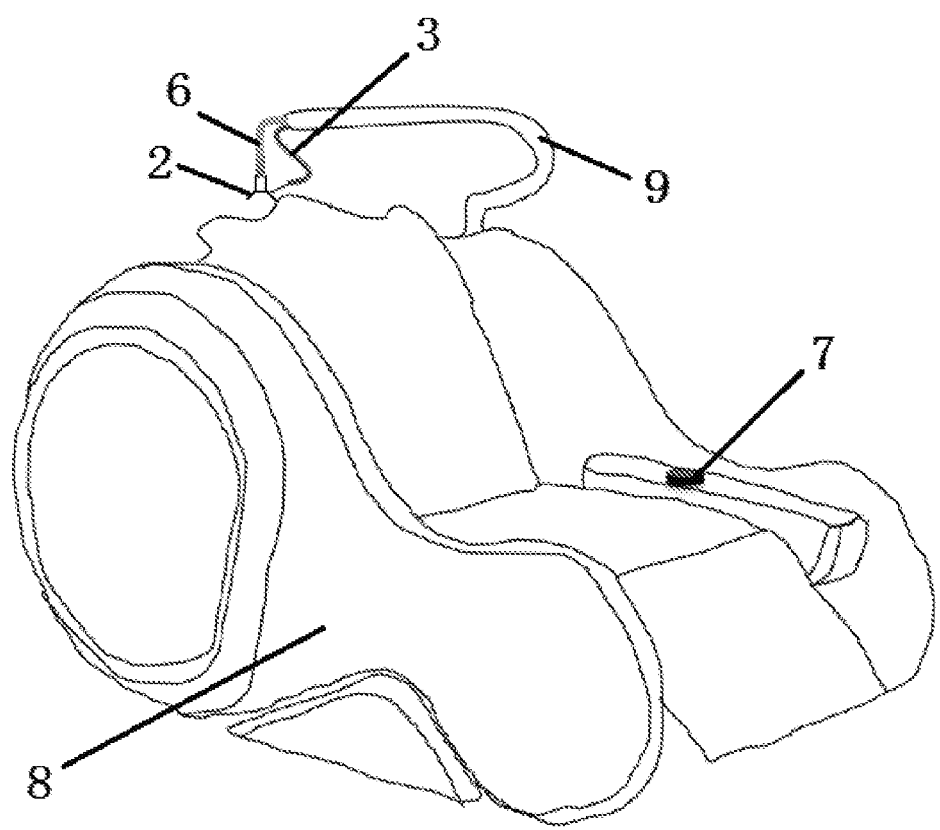
FIG. 2 is a schematic diagram showing that a perimeter of the present invention cooperates with a multifunctional chair.
Figure 4:
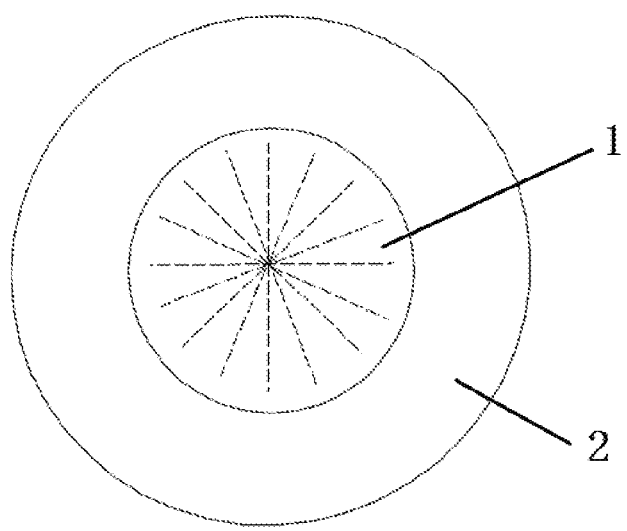
FIG. 4 is a schematic diagram when watching a screen.

Embodiment 1, referring to FIGS. 1-2 and 4, the perimeter includes a projection screen 1, a computer (control center) for controlling an image displayed on the projection screen 1, and a feedback device for recording feedback information. The perimeter further includes a negative pressure ring 2, a negative pressure tube 3 connected to the negative pressure ring 2, and an observation cylinder 4 in the middle of the negative pressure ring. The observation cylinder 4 is provided with an observation hole in the center, one end of the observation cylinder 4 is connected to the middle of the negative pressure ring 2, and the projection screen 1 is fixedly arranged at the other end of the observation cylinder. A lens set is disposed in the observation hole, the projection screen 1 is connected to a perimetry display device (not shown) through light guide fibers 6, and the projection screen 1 projects and displays the content displayed by the perimetry display device. The negative pressure tube 3 is connected to a negative pressure pump (not shown). The negative pressure pump provides an adsorption force for the negative pressure ring, so that the negative pressure ring 2 can be reliably adsorbed to the eyeball. The main function of the lens set 5 is to correct the refractive status of a patient, so that the patient can clearly gaze at the image on the projection screen 1. The content on the projection screen 1 can be changed by changing the content displayed by the perimetry display device through the computer to obtain different images. FIG. 2 shows an embodiment in which the perimeter of the present invention is arranged on a multifunctional chair. When a patient is tested for the field of view, the angle of a backrest of the multifunctional chair 8 can be adjusted, and a support rod 9 is adjusted to be directly above the patient's eye. The image type, intensity, stimulation frequency, stimulation time, etc. on the perimetry display device are controlled by the computer, the negative pressure ring 2 is adsorbed to the eyeball, and the patient gazes at the image projected by the light guide fibers 6, and presses a button 7 when seeing the image, recorded as +. If the button 7 is not pressed, that is, the patient does not see the image, recorded as −. All feedback information is fed back to a signal collector for result calculation and recording, and the patient's field of view is finally exported. It should be noted that the signal collector may be the computer or a separate mechanism.

Figure 3:
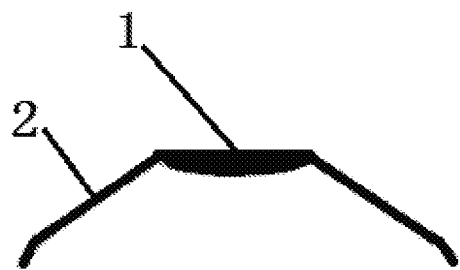
FIG. 3 is a schematic diagram of a variant of the adsorption device.

Embodiment 2, referring to FIG. 3 and FIG. 4, the negative pressure ring 2 is provided with a hole in the middle, and the projection screen 1 is directly fixed to the circular hole. The projection screen 1 is connected with light guide fibers 6, and in this mode, the other ends of the light guide fibers are directly connected to point light sources. Each bundle of light guide fibers is an independent stimulation point which is connected to an independent point light source. The dotted line in FIG. 4 shows the distribution of the light guide fibers. The position and intensity of stimulating light on the projection screen are adjusted by controlling each point light source. The negative pressure ring is adsorbed to the eyeball by self-adsorption, or adsorbed to the eyeball by means of a negative pressure pump. Due to the self-adsorption, the mechanisms such as a negative pressure tube and a negative pressure pump are removed, which is beneficial to simplifying the adsorption device. Optionally, a transparent layer may be provided at the hole to isolate the eyeball from the screen so as to avoid direct contact of the eyeball with the screen. It should be noted that the projection screen 1 may be removed, the light guide fibers are arranged in a certain way and connected to the fixation forcing device, and the other ends are connected to point light sources to directly project light points of the point light sources into the eye, where such an arrangement may be scattering from the center to four sides as shown in FIG. 4.

In the above technical solution, for the objective perimeter, the feedback device is replaced with an electro-physiological examination instrument (not shown) for recording an electro-physiological signal generated when a testee observes an image on the perimetry display device, so that the testee's field of view is examined, the patient does not need to respond to the stimulation, and objective examination is achieved.

It should be noted that the perimeter of the present invention may be used alone, and is not necessarily arranged on the multifunctional chair; the projection screen may also be a curved screen more fitting to the eyeball, such as an OLED screen; the observation area on the fixation forcing device may be set in any shape; the fixation forcing device is not necessarily limited to a ring, as long as the fixation forcing device can be adsorbed to the eyeball and the display conduction device is fixed to the fixation forcing device.

According to the perimeter of the present invention, the fixation forcing device is adsorbed to the eyeball, and moves synchronously when the eyeball moves, so that the eyeball always gazes at the same position of the perimetry display device, that is, the eye gaze position is fixed relative to the perimetry display device. The conventional perimeter requires the patient to try to gaze at the center of the perimetry display device so as to achieve relative fixation of the eye gaze position and the position of the perimetry display device, and in this process, the patient is always distracted, causing deviations in the examination result. After the fixation forcing device of the present perimeter is used, the patient passively gazes at the same position of the perimetry display device in the whole examination process, thereby eliminating the distraction caused by active gaze, and improving the cooperation of the patient during examination and the accuracy of the examination result. The display conduction device is formed by arranging light guide fibers to conduct images. The feedback device of the perimeter may be a conventional press-type feedback device. The feedback device may also be an electro-physiological examination instrument, that is, an objective perimeter, and in this mode, the patient does not need to make any response, so that the subjective cooperation factor of the patient is completely eliminated, and the perimeter is completely transformed into an objective examination device, which is another major breakthrough of the perimeter.

The invention claimed is:

1. A perimeter, comprising a fixation forcing device, a display conduction device, a perimetry display device, a feedback device for recording feedback information, and a control center for controlling the perimetry display device and collecting feedback information, wherein the fixation forcing device is used for forcing the eyeball in a fixation state during perimetry, and the display conduction device is connected to the fixation forcing device and the perimetry display device respectively.

2. The perimeter according to claim 1, wherein the fixation forcing device comprises a negative pressure ring, a hole is formed in the middle of the negative pressure ring, and the display conduction device is fixedly arranged at the hole.

3. The perimeter according to claim 1, wherein the display conduction device comprises light guide fibers, the light guide fibers are arranged in a certain way and connected to the fixation forcing device, and the other ends are connected to point light sources to directly project light points of the point light sources into the eye.

4. The perimeter according to claim 1, wherein the display conduction device comprises a projection screen and light guide fibers connected to the projection screen, the projection screen is connected to the fixation forcing device, one ends of the light guide fibers are connected to the projection screen, and the other ends are connected to the perimetry display device to project an image on the perimetry display device into the eye.

5. The perimeter according to claim 1, wherein the feedback device is a press-type touch feedback device.

6. The perimeter according to claim 1, wherein the feedback device is an electro-physiological examination instrument for recording an electro-physiological signal generated when a testee observes an image on the perimetry display device.

7. The perimeter according to claim 1, wherein the control center is a computer loaded with an artificial intelligence algorithm, and can automatically perform personalized display adjustment according to the age of the patient and the previous examination status and perform personalized processing on the collected feedback data.

* * * * *